US010935310B2

(12) United States Patent
Junge et al.

(10) Patent No.: US 10,935,310 B2
(45) Date of Patent: Mar. 2, 2021

(54) INVENTORY SYSTEM FOR A REFRIGERATOR APPLIANCE

(71) Applicant: Haier US Appliance Solutions, Inc., Wilmington, DE (US)

(72) Inventors: Brent Alden Junge, Evansville, IN (US); John Keith Besore, Prospect, KY (US); Michael C. Watanabe, Louisville, KY (US)

(73) Assignee: Haier US Appliance Solutions, Inc., Wilmington, DE (US)

( * ) Notice: Subject to any disclaimer, the term of this patent is extended or adjusted under 35 U.S.C. 154(b) by 197 days.

(21) Appl. No.: 15/983,190

(22) Filed: May 18, 2018

(65) Prior Publication Data

US 2019/0353421 A1   Nov. 21, 2019

(51) Int. Cl.
| | | |
|---|---|---|
| *F25D 25/02* | (2006.01) | |
| *F25D 23/12* | (2006.01) | |
| *G01N 33/02* | (2006.01) | |
| *G01G 19/414* | (2006.01) | |
| *F25D 29/00* | (2006.01) | |

(52) U.S. Cl.
CPC .......... *F25D 29/005* (2013.01); *F25D 23/12* (2013.01); *F25D 25/02* (2013.01); *G01G 19/414* (2013.01); *G01N 33/02* (2013.01); *F25D 2400/36* (2013.01); *F25D 2400/40* (2013.01); *F25D 2700/06* (2013.01); *F25D 2700/08* (2013.01)

(58) Field of Classification Search
CPC ....... G01N 33/02; F25D 29/005; F25D 23/12; F25D 25/02; F25D 2700/08; F25D 2400/40; F25D 2400/36; F25D 2700/06; G01G 19/414; G01G 19/42

USPC ............................................................ 177/1
See application file for complete search history.

(56) References Cited

U.S. PATENT DOCUMENTS

| | | | |
|---|---|---|---|
| 7,432,454 B1 | 10/2008 | Sze et al. | |
| 7,861,542 B2 | 1/2011 | Rozendaal et al. | |
| 9,175,904 B2* | 11/2015 | Allard | F25D 25/025 |
| 9,449,208 B2* | 9/2016 | Luk | F25D 29/005 |
| 9,784,497 B2* | 10/2017 | Wang | F25D 29/00 |
| 10,203,678 B2* | 2/2019 | Lagares-Greenblatt | A23L 3/003 |

(Continued)

FOREIGN PATENT DOCUMENTS

| | | |
|---|---|---|
| CN | 105444504 A | 3/2016 |
| CN | 205825571 U | 12/2016 |
| JP | H109753 A | 1/1998 |

(Continued)

OTHER PUBLICATIONS

Smart Refrigerator Using Internet, Journal of Multidisciplinary Engineering Science and Technology (JMEST) ISSN: 3159-0040, Prapulla et al. (Year: 2015).*

*Primary Examiner* — Jacques M Saint Surin
(74) *Attorney, Agent, or Firm* — Dority & Manning, P.A.

(57) ABSTRACT

An inventory system for a refrigerator appliance includes an inventory plate which is operably coupled to a load cell and positioned within a chilled chamber. The inventory plate may be a fixed shelf or a portable coaster on which food items may be placed. A controller is configured for monitoring a weight of the food items over time using the load cell and/or a moisture content using a moisture sensor and providing an indication of food quality based at least in part on the weight and/or moisture content of the food items.

20 Claims, 7 Drawing Sheets

(56) References Cited

U.S. PATENT DOCUMENTS 10,467,584 B2 * 11/2019 Lee .................. G06K 9/6253
2017/0100495 A1    4/2017 Shur et al.

FOREIGN PATENT DOCUMENTS

| KR | 20120118376 A | 10/2012 |
| WO | WO2016087084 A1 | 6/2016 |
| WO | WO2017180752 A1 | 10/2017 |

* cited by examiner

INVENTORY SYSTEM FOR A REFRIGERATOR APPLIANCE

FIELD OF THE INVENTION

The present subject matter relates generally to refrigerator appliances, and more particularly to inventory control systems for refrigerator appliances.

BACKGROUND OF THE INVENTION

Refrigerator appliances generally include a cabinet that defines a chilled chamber for receipt of food articles for storage. In addition, refrigerator appliances include one or more doors rotatably hinged to the cabinet to permit selective access to food items stored in chilled chamber(s). It is frequently desirable to monitor food items within the chilled chamber, e.g., to know when they are added to or removed from the chilled chambers or to monitor the food quality. For example, it may be desirable to know when a particular food article needs to be added to a shopping list so that is may be resupplied, when food has reached its optimal ripeness, or when food has spoiled and should be thrown out.

Certain conventional refrigerator appliances include camera systems for monitoring food placed therein. However, camera systems require costly image recognition systems, are very sensitive to viewing angles, and are difficult to use when the appliance is fully loaded. Alternatively, some appliances require scanning food items (e.g., using a barcode or a radio frequency identification device) as the food items are added into or removed from the refrigerator to provide the appliance with knowledge of the food stored therein. However, such systems are costly, rely on the availability of compatible food products or packaging, and require too much effort by the consumer for proper functioning.

Accordingly, an improved inventory control system for a refrigerator appliance would be useful. More particularly, a refrigerator appliance including a simple, intuitive, and effective system for informing a user of useful information for inventory management would be particularly beneficial.

BRIEF DESCRIPTION OF THE INVENTION

Aspects and advantages of the invention will be set forth in part in the following description, or may be apparent from the description, or may be learned through practice of the invention.

In a first exemplary embodiment, a refrigerator appliance is provided including a cabinet defining a chilled chamber and a door being rotatably hinged to the cabinet to provide selective access to the chilled chamber. An inventory plate receives food items for storage within the chilled chamber, the inventory plate being operably coupled to a load cell. A controller is operably coupled to the load cell and is configured for monitoring a weight of the food items over time using the load cell and providing an indication of food quality based at least in part on the weight of the food items.

According to another exemplary embodiment, a method of operating a refrigerator appliance is provided. The refrigerator appliance includes a cabinet defining a chilled chamber and a door rotatably hinged to the cabinet to provide selective access to the chilled chamber. The method includes receiving food items for storage on an inventory plate positioned within the chilled chamber, the inventory plate being operably coupled to a load cell. The method further includes monitoring a weight of the food items over time using the load cell and providing an indication of food quality based at least in part on the weight of the food items.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures.

Figure 1:
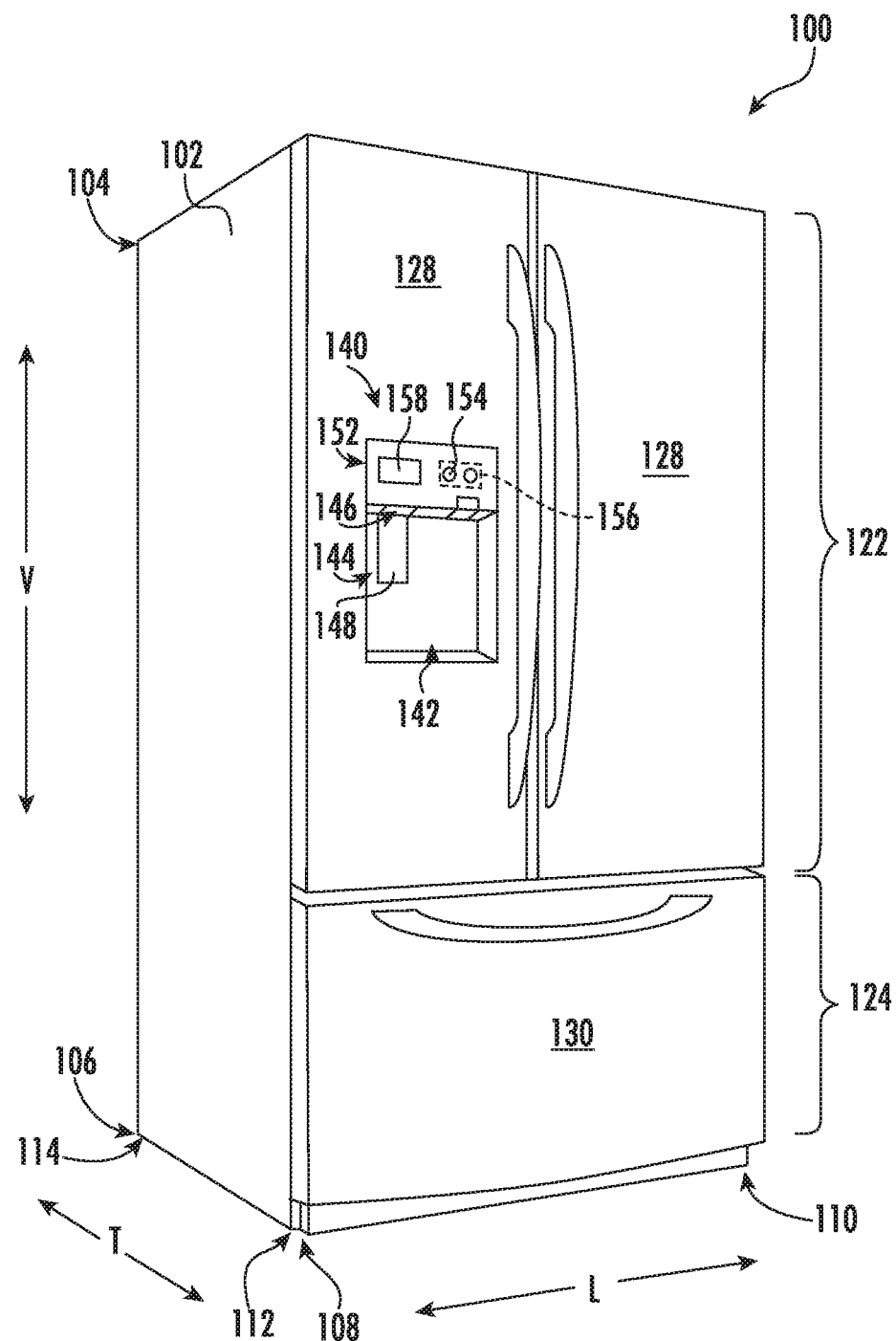
FIG. 1 provides a perspective view of a refrigerator appliance according to an exemplary embodiment of the present subject matter.

Repeat use of reference characters in the present specification and drawings is intended to represent the same or analogous features or elements of the present invention.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

FIG. 1 provides a perspective view of a refrigerator appliance 100 according to an exemplary embodiment of the present subject matter. Refrigerator appliance 100 includes a cabinet or housing 102 that extends between a top 104 and a bottom 106 along a vertical direction V, between a first side 108 and a second side 110 along a lateral direction L, and between a front side 112 and a rear side 114 along a transverse direction T. Each of the vertical direction V, lateral direction L, and transverse direction T are mutually perpendicular to one another.

Housing 102 defines chilled chambers for receipt of food items for storage. In particular, housing 102 defines fresh food chamber 122 positioned at or adjacent top 104 of housing 102 and a freezer chamber 124 arranged at or adjacent bottom 106 of housing 102. As such, refrigerator appliance 100 is generally referred to as a bottom mount refrigerator. It is recognized, however, that the benefits of the present disclosure apply to other types and styles of refrigerator appliances such as, e.g., a top mount refrigerator appliance, a side-by-side style refrigerator appliance, or a single door refrigerator appliance. Consequently, the description set forth herein is for illustrative purposes only and is not intended to be limiting in any aspect to any particular refrigerator chamber configuration.

Refrigerator doors 128 are rotatably hinged to an edge of housing 102 for selectively accessing fresh food chamber 122. In addition, a freezer door 130 is arranged below refrigerator doors 128 for selectively accessing freezer chamber 124. Freezer door 130 is coupled to a freezer drawer (not shown) slidably mounted within freezer chamber 124. Refrigerator doors 128 and freezer door 130 are shown in the closed configuration in FIG. 1. One skilled in the art will appreciate that other chamber and door configurations are possible and within the scope of the present invention.

Figure 2:
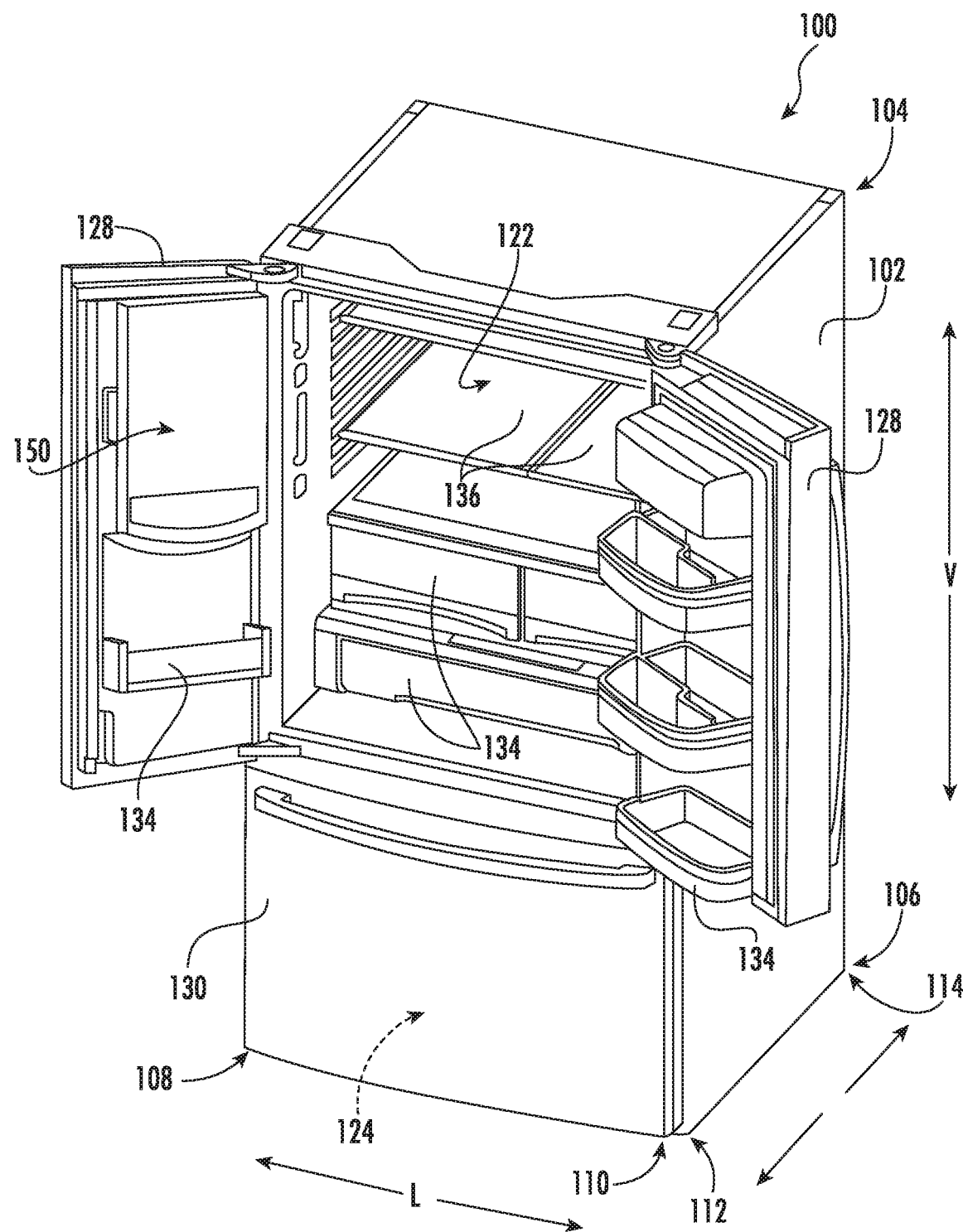
FIG. 2 provides a perspective view of the exemplary refrigerator appliance of FIG. 1, with the doors of the fresh food chamber shown in an open position.

FIG. 2 provides a perspective view of refrigerator appliance 100 shown with refrigerator doors 128 in the open position. As shown in FIG. 2, various storage components are mounted within fresh food chamber 122 to facilitate storage of food items therein as will be understood by those skilled in the art. In particular, the storage components may include bins 134 and shelves 136. Each of these storage components are configured for receipt of food items (e.g., beverages and/or solid food items) and may assist with organizing such food items. As illustrated, bins 134 may be mounted on refrigerator doors 128 or may slide into a receiving space in fresh food chamber 122. It should be appreciated that the illustrated storage components are used only for the purpose of explanation and that other storage components may be used and may have different sizes, shapes, and configurations.

Referring again to FIG. 1, a dispensing assembly 140 will be described according to exemplary embodiments of the present subject matter. Although several different exemplary embodiments of dispensing assembly 140 will be illustrated and described, similar reference numerals may be used to refer to similar components and features. Dispensing assembly 140 is generally configured for dispensing liquid water and/or ice. Although an exemplary dispensing assembly 140 is illustrated and described herein, it should be appreciated that variations and modifications may be made to dispensing assembly 140 while remaining within the present subject matter.

Dispensing assembly 140 and its various components may be positioned at least in part within a dispenser recess 142 defined on one of refrigerator doors 128. In this regard, dispenser recess 142 is defined on a front side 112 of refrigerator appliance 100 such that a user may operate dispensing assembly 140 without opening refrigerator door 128. In addition, dispenser recess 142 is positioned at a predetermined elevation convenient for a user to access ice and enabling the user to access ice without the need to bend-over. In the exemplary embodiment, dispenser recess 142 is positioned at a level that approximates the chest level of a user.

Dispensing assembly 140 includes an ice dispenser 144 including a discharging outlet 146 for discharging ice from dispensing assembly 140. An actuating mechanism 148, shown as a paddle, is mounted below discharging outlet 146 for operating ice or water dispenser 144. In alternative exemplary embodiments, any suitable actuating mechanism may be used to operate ice dispenser 144. For example, ice dispenser 144 can include a sensor (such as an ultrasonic sensor) or a button rather than the paddle. Discharging outlet 146 and actuating mechanism 148 are an external part of ice dispenser 144 and are mounted in dispenser recess 142. By contrast, refrigerator door 128 may define an icebox compartment 150 (FIG. 2) housing an icemaker and an ice storage bin (not shown) that are configured to supply ice to dispenser recess 142.

A control panel 152 is provided for controlling the mode of operation. For example, control panel 152 includes one or more selector inputs 154, such as knobs, buttons, touchscreen interfaces, etc., such as a water dispensing button and an ice-dispensing button, for selecting a desired mode of operation such as crushed or non-crushed ice. In addition, inputs 154 may be used to specify a fill volume or method of operating dispensing assembly 140. In this regard, inputs 154 may be in communication with a processing device or controller 156. Signals generated in controller 156 operate refrigerator appliance 100 and dispensing assembly 140 in response to selector inputs 154. Additionally, a display 158, such as an indicator light or a screen, may be provided on control panel 152. Display 158 may be in communication with controller 156, and may display information in response to signals from controller 156.

As used herein, "processing device" or "controller" may refer to one or more microprocessors or semiconductor devices and is not restricted necessarily to a single element. The processing device can be programmed to operate refrigerator appliance 100 and dispensing assembly 140. The processing device may include, or be associated with, one or more memory elements (e.g., non-transitory storage media). In some such embodiments, the memory elements include electrically erasable, programmable read only memory (EEPROM). Generally, the memory elements can store information accessible processing device, including instructions that can be executed by processing device. Optionally, the instructions can be software or any set of instructions and/or data that when executed by the processing device, cause the processing device to perform operations.

Figure 3:
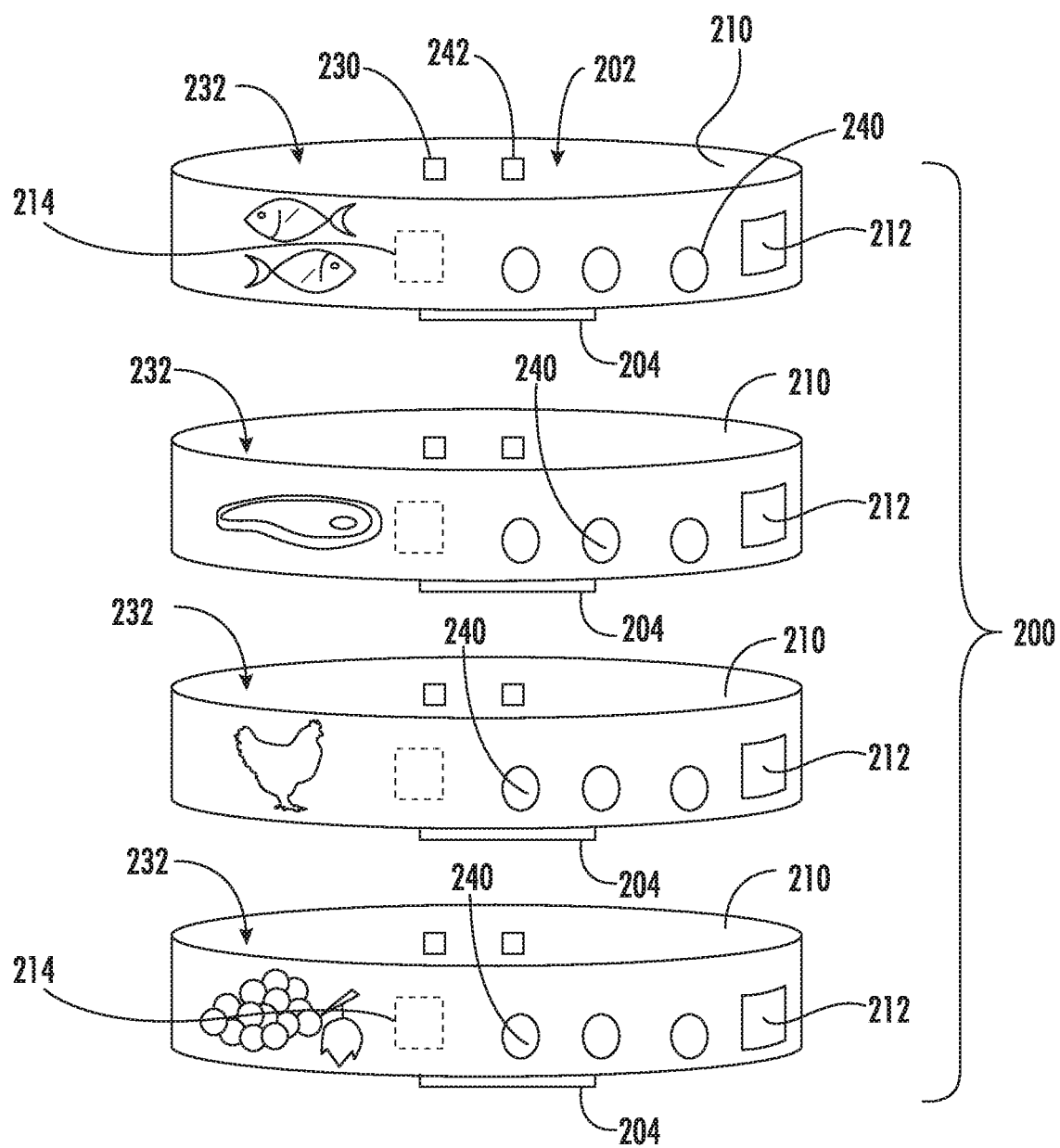
FIG. 3 provides a schematic view of portable coasters of an inventory control system for use with the exemplary refrigerator appliance of FIG. 1 according to an exemplary embodiment of the present subject matter.
Figure 4:
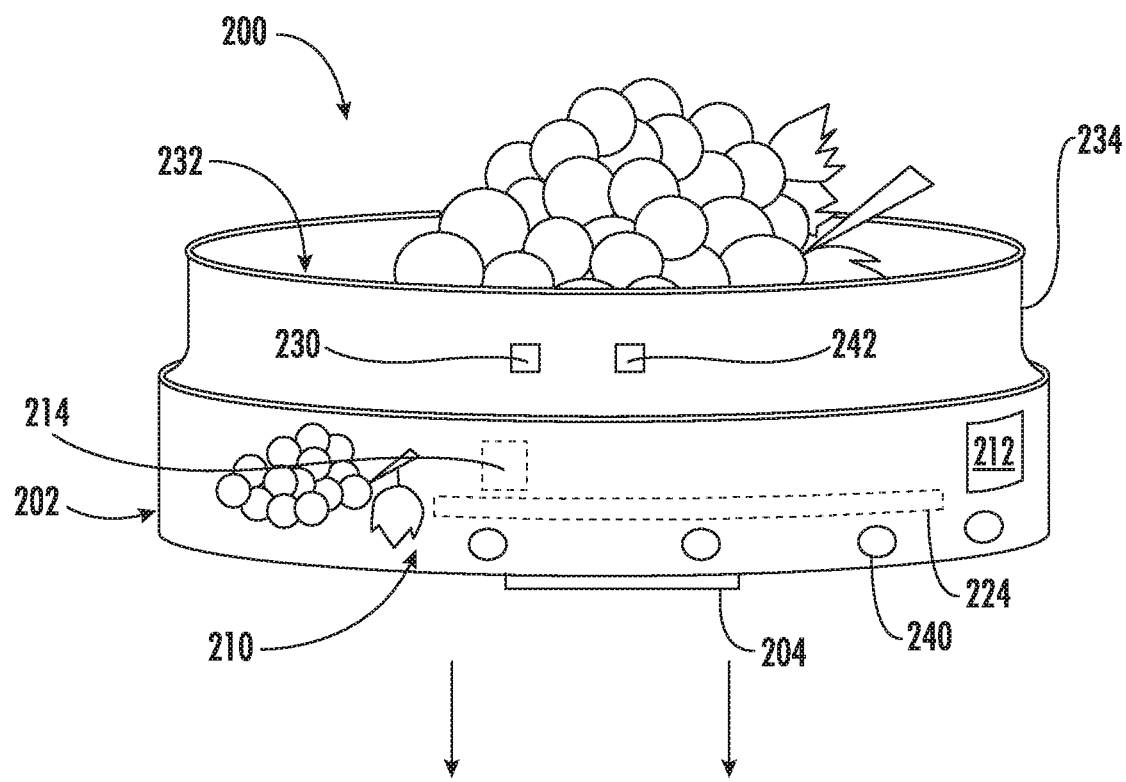
FIG. 4 provides a perspective view of a portable coaster of the exemplary inventory control system of FIG. 3 according to another exemplary embodiment of the present subject matter.
Figure 4:
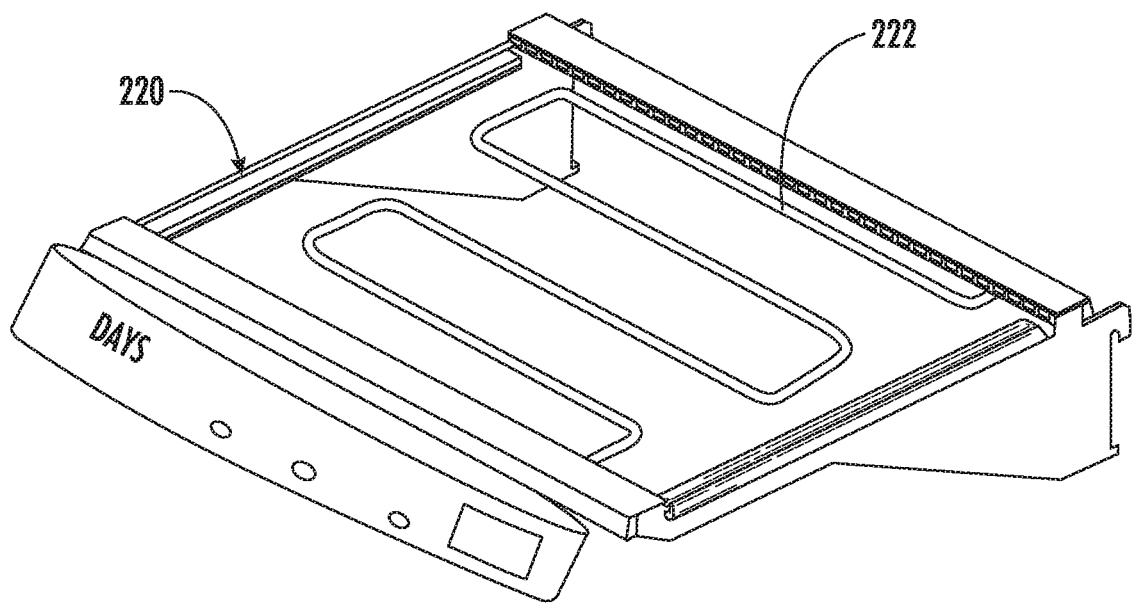
Figure 5:
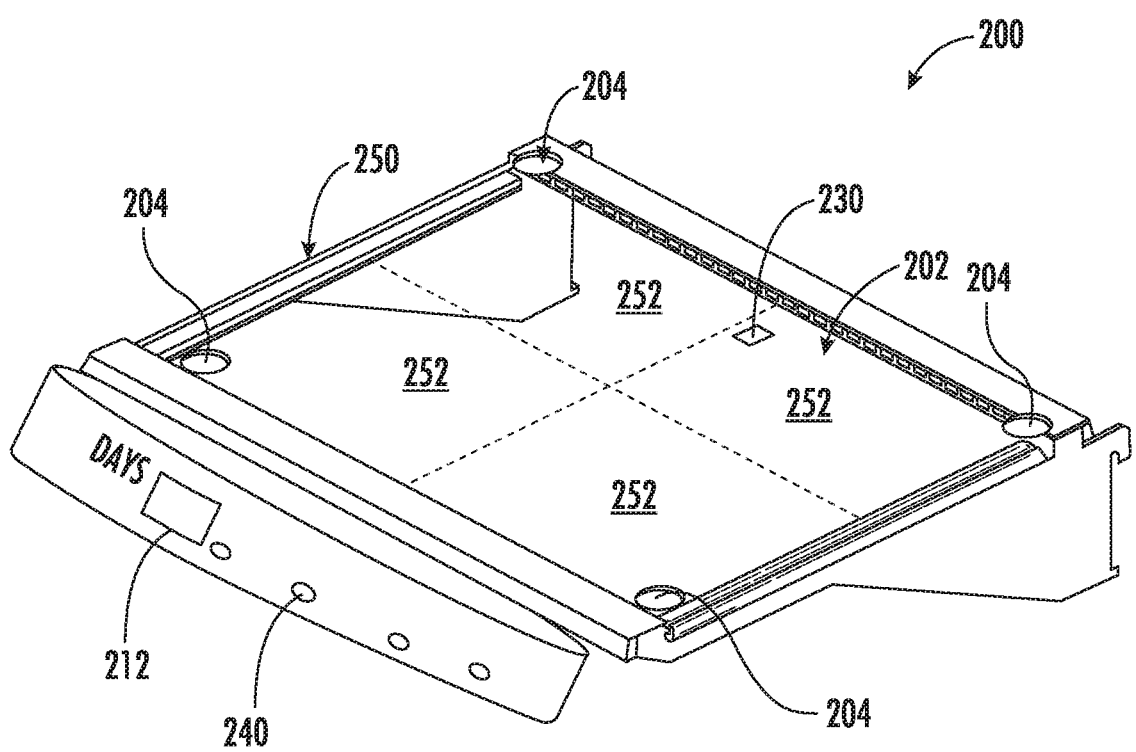
FIG. 5 illustrates a shelf for use with the exemplary inventory control system of FIG. 3 according to an exemplary embodiment of the present subject matter.

Referring now to FIGS. 3 through 5, an inventory control system 200 that may be used with refrigerator appliance 100 will be described according to an exemplary embodiment of the present subject matter. In general, inventory control system 200 is used for monitoring food items positioned within a chilled chamber (e.g., fresh food chamber 122 or freezer chamber 124) of refrigerator appliance 100. More specifically, inventory control system 200 may be used to detect and monitor the addition or removal of food items, the quality of food items, the spoilage of food items, the ripeness of food items, and other quality-related aspects of food items. In addition, inventory control system 200 may be used to provide information to a user of refrigerator appliance 100 regarding the monitored food items. An exemplary system and method of use are described below for the purposes of explanation. However, it should be appreciated that modifications and variations may be made to inventory control system 200 while remaining within scope of the present subject matter.

As used herein, "food items" may be used to refer to any perishable or nonperishable food or drink that may be consumed by a user of refrigerator appliance 100. For example, food items may refer to fruits, vegetables, beef, poultry, fish, drinks, or any other suitable item typically positioned within a refrigerator appliance. The monitoring algorithms described herein may be adapted to the particular type of food item. In addition, "food quality" and related terms are used generally to refer to a condition of the food items. For example, food quality may refer to the amount of time that a particular food item has been positioned within the refrigerator, the level of the ripeness of a particular food item, a moisture content of a particular food item, or any other quality characteristic associated with food or drinks.

In general, inventory control system 200 includes an inventory plate 202 for receiving food items for storage within a chilled chamber, e.g., fresh food chamber 122. The inventory plate 202 may be operably coupled to a weight sensor or load cell 204 for measuring a weight of food items positioned on inventory plate 202. In this regard, inventory control system 200, inventory plate 202, and load cell 204 may be generally coupled to a controller (e.g., such as controller 156) for monitoring and operating inventory control system 200. Thus, for example, when a food item is positioned on inventory plate 202, load cell 204 detects a change in weight and may begin tracking the quality of food item.

Referring now specifically to FIGS. 3 and 4, inventory plate 202 may comprise or be embodied as one or more portable coasters 210 according to an exemplary embodiment. Portable coasters 210 may be positioned within fresh food chamber 122, e.g., on a shelf 136 or within a bin 134, and food items may be positioned on top of portable coasters 210. Load cell 204 within portable coasters 210 may monitor the weight of the food items over time (see, e.g., FIG. 7) for monitoring food quality. According to an exemplary embodiment, refrigerator appliance 100 may include a plurality of portable coasters 210, and each portable coaster 210 may be configured for receiving a particular type of food item, such as fish, beef, poultry, fruits, or vegetables. By contrast, portable coasters 210 could alternatively include a user input button 212 which a user may press to indicate the type of food items positioned on portable coaster 210.

In addition according to one exemplary embodiment, portable coaster 210 may include an identification chip, such as a radio frequency identification device (RFID) tag 214. The RFID tag 214 may be used to communicate information with controller 156. For example, the RFID tag 214 may communicate a timestamp of when food is added, the type of food added, a coaster identification code, or any other information related to the food items or the coaster itself.

Notably, because portable coasters 210 are by definition not connected to refrigerator appliance 100 by electrical wires, a means for powering portable coasters 210 is desirable. According to one embodiment, portable coasters 210 may be battery-powered. By contrast, according to the illustrated embodiment, portable coasters 210 may be powered by induction through refrigerator appliance 100. For example, refrigerator appliance 100 may include an induction shelf 220 (e.g., such as shelf 136) that is positioned within fresh food chamber 122 and includes one or more induction coils 222. In addition, portable coaster 210 may have an induction plate 224 for receiving power from induction coils 222 when positioned on induction shelf 220 or otherwise positioned within the electromagnetic field generated by induction coils 222.

In addition to monitoring the weight of food items, inventory plate 202 may include features for monitoring the moisture of food items. In this regard, for example, portable coasters 210 may include moisture sensors 230 for monitoring the moisture of food items positioned on portable coasters 210. In this regard, for example, moisture sensor 230 may be positioned on a top surface 232 of each portable coaster 210 such that moisture the drips from food items contacts moisture sensor 230. In addition, each portable coaster may define a raised edge or ridge 234 for containing moisture on portable coaster 210. Thus, as food items lose their moisture over time, the moisture may collect on portable coaster 210, and moisture sensor 230 may be used to provide an indication of food quality. In addition, moisture sensor 230 may be used to detect leaks and send an appropriate message to a user of the appliance.

In addition, inventory control system 200 may generally include one or more displays 240 which are used to provide a user of refrigerator appliance 100 with an indication or notification regarding food quality of food items or other information related to the food items. According to one embodiment, this food quality information may be displayed on the appliance display 158. Alternatively, display 240 may be on each portable coaster 210. For example, according to the illustrated embodiment, display 240 may include a plurality of light emitting diodes (LEDs) which are used to indicate some aspect of food quality. Alternatively, portable coasters 210 may include a touchscreen or other interactive display which a user may use to control inventory control system 200 or for providing information to a user regarding food items or their quality.

Still referring to FIGS. 3 and 4, portable coasters 210 may include a light sensor 242 which is configured for detecting when door 128 of refrigerator appliance 100 has been closed. In this manner, when light sensor 242 detects no more light, display 240 may be turned off and other power saving features of portable coasters 210 may be activated to reduce energy usage. When a user opens refrigerator door 128, light sensor 242 detects the light and powers portable coaster 210 and display 240.

Referring now to FIG. 5, inventory plate 202 will be described according to an alternative embodiment of the present subject matter. According to this embodiment, inventory plate 202 may be a monitoring shelf 250 (e.g., such as shelf 136 of refrigerator appliance 100) that is positioned within a chilled chamber (e.g., such as fresh food compartment 122). Due to the similarity of features between monitoring shelf 250 and portable coasters 210, like reference numerals may be used to refer to similar features herein.

As illustrated, monitoring shelf 250 is supported by four load cells 204, though fewer or more cells may be used according to alternative embodiments. Load cells 204 may be generally configured for detecting and monitoring food items positioned on monitoring shelf 250. More specifically, according to the illustrated embodiment, monitoring shelf 250 may define a plurality of zones 252 which are configured for receiving different food items or types of food items. Controller 156 may be configured for detecting where a food item is positioned on monitoring shelf 250 based on the distribution of weight detected by the one or more of cells 204. Thus, for example, one zone 252 of monitoring shelf 250 may be configured for receiving fruits. When a bag of grapes is positioned within the zone 252 on monitoring shelf 250, load cells 204 can detect that the grapes of have been positioned within the fruit zone, may identify the food item as fruits, and may implement a fruit specific monitoring algorithm. According to the illustrated embodiment, monitoring shelf 250 is directly wired to refrigerator appliance 100 for power and is directly coupled to controller 156.

Now that the construction and configuration of refrigerator appliance 100 and inventory control system 200 have been described according to an exemplary embodiment of the present subject matter, an exemplary method 300 for operating a refrigerator appliance and an inventory control system according to an exemplary embodiment of the present subject matter is provided. Method 300 can be used by a manufacturer to operate inventory control system 200, or any other suitable refrigerator appliance inventory system. It should be appreciated that the exemplary method 300 is discussed herein only to describe exemplary aspects of the present subject matter, and is not intended to be limiting.

Figure 6:
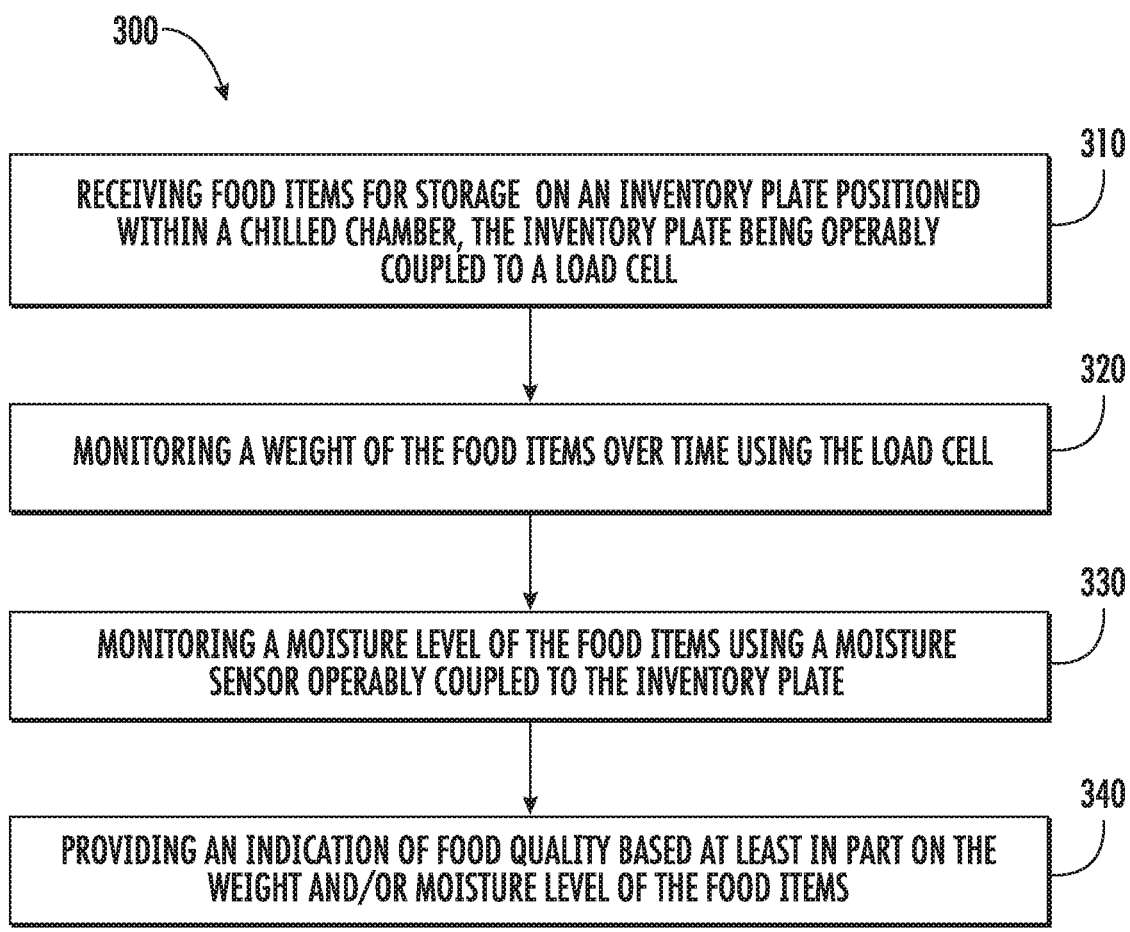
FIG. 6 is a method of operating a refrigerator appliance to monitor food quality of food items placed therein according to an exemplary embodiment of the present subject matter.

Referring now to FIG. 6, method 300 includes, at step 310, receiving food items for storage on an inventory plate positioned within a chilled chamber. Continuing the example from above, the inventory plate may be a portable coaster or a monitoring shelf mounted within a refrigerator appliance. In addition, the inventory plate may be operably coupled to a load cell for detecting a weight of food items positioned on the inventory plate. In addition, the inventory plate may include a moisture sensor for detecting the moisture of food items.

Step 320 includes monitoring a weight of the food items over time using the load cell. In addition, step 330 includes monitoring a moisture level of the food items using the moisture sensor. The controller of the inventory control system may include a variety of monitoring algorithms for using the weight and moisture measurements to determine a food quality characteristic of the food items positioned on the inventory plate. Step 240 includes providing an indication of food quality based at least in part on the weight and/or the moisture level of the food items to a user of the appliance.

FIG. 6 depicts steps performed in a particular order for purposes of illustration and discussion. Those of ordinary skill in the art, using the disclosures provided herein, will understand that the steps of any of the methods discussed herein can be adapted, rearranged, expanded, omitted, or modified in various ways without deviating from the scope of the present disclosure. Moreover, although aspects of method 300 are explained using refrigerator appliance 100 and inventory control system 200 as an example, it should be appreciated that these methods may be applied to any suitable inventory control system.

Figure 7:
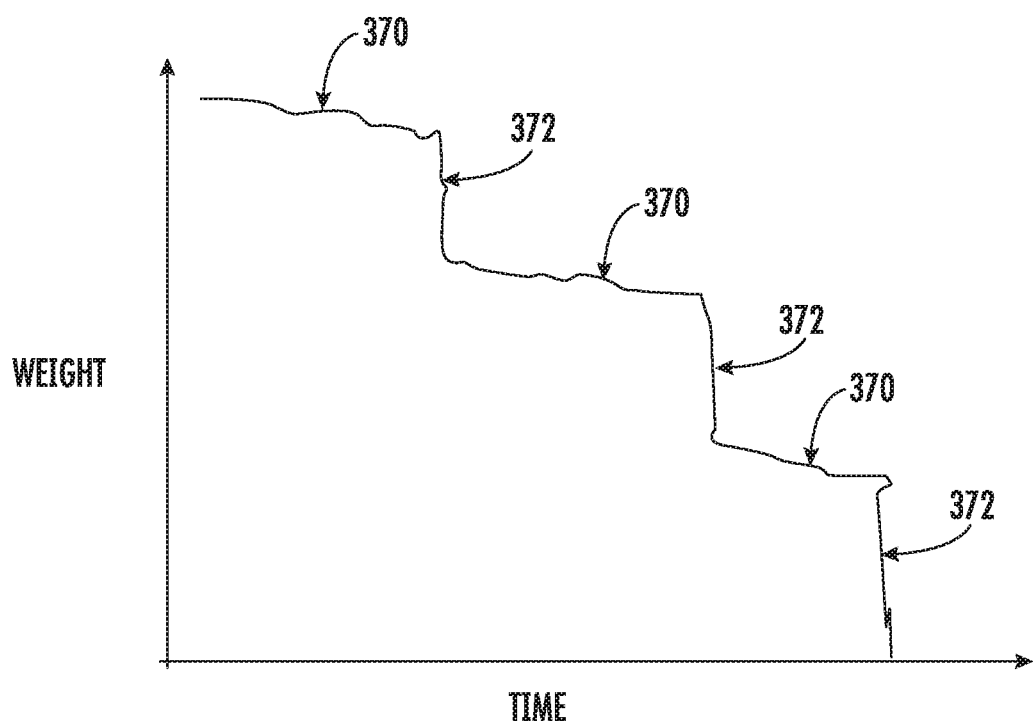
FIG. 7 is a plot illustrating the weight of a particular food item over time according to another exemplary embodiment of the present subject matter.

As an example, referring to FIG. 7, the weight of food items placed on portable coaster 210 over time will be described. Specifically, for example, the food item may be a batch of grapes. Notably, grapes and many other perishable foods contain greater than 80% water when fresh. As these food items age, moisture within the food escapes by evaporation. Thus when fresh grapes are placed on portable coaster 210 the weight is at the highest point shown in FIG. 7. Controller 156 may be configured for detecting normal weight loss due to evaporation and distinguishing it from the consumption of grapes, e.g. by monitoring the slope of the weight/time plot in FIG. 7. In this regard, for example, the slope of the plot indicates evaporation is occurring at regions 370 and consumption has occurred at regions 372 (indicating step change in weight). The water loss due to evaporation may be calculated from the slope in evaporation regions 370 and may be used to deduce a quality of the remaining grapes. This information is provided to the user in the form of an indication to finish the grapes or throw them out because they are spoiled.

According to alternative embodiments, inventory control system 200 may rely in whole or in part on a timer based monitoring system. In this regard, for example, when a food item is positioned on portable coaster 210, the portable coaster 210 may obtain information regarding the lifetime of that food item from fresh to spoiled. The type of food item may be determined from the coaster type, by a user input, by a weight, or by any other suitable means. When the timer has expired, inventory control system 200 may provide an indication to a user of refrigerator appliance 100 that the particular food item needs to be thrown out. For example, the indication may be provided by display 240 on portable coaster 210 or by display 158 of refrigerator appliance 100. When the food item is finished, thrown out, or replaced, the timer may be reset by pressing user input button 212, or after a specific amount of time has lapsed with no food on portable coaster 210.

As one skilled in the art will appreciate, the above described embodiments are used only for the purpose of explanation. Modifications and variations may be applied, other configurations may be used, and the resulting configurations may remain within the scope of the invention. For example, inventory plate 202 may be positioned at any suitable location and may include any suitable number and type of sensors. In addition, the control and monitoring algorithms may be adapted to provide appropriate indications or information regarding any suitable type or quantity of food. One skilled in the art will appreciate that such modification and variations may remain within the scope of the present subject matter.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A refrigerator appliance comprising:
   a cabinet defining a chilled chamber;
   a shelf positioned within the chilled chamber;
   one or more induction coils mounted to the shelf;
   a door being rotatably hinged to the cabinet to provide selective access to the chilled chamber;
   an inventory plate for receiving food items for storage within the chilled chamber, the inventory plate comprising a portable coaster having an induction plate mounted within for receiving power from the one or more induction coils when the portable coaster is positioned on the shelf, the inventory plate being operably coupled to a load cell; and
   a controller operably coupled to the load cell, the controller being configured for:
      monitoring a weight of the food items over time using the load cell; and
      providing an indication of food quality based at least in part on the weight of the food items.

2. The refrigerator appliance of claim 1, wherein the refrigerator appliance comprises:

a plurality of portable coasters, each of the coasters being configured for storing and monitoring a particular type of food item.

3. The refrigerator appliance of claim 1, wherein the portable coaster comprises:
a radio frequency identification device (RFID) tag for communicating information with the controller.

4. The refrigerator appliance of claim 1, wherein the portable coaster is battery powered.

5. The refrigerator appliance of claim 1, wherein the inventory plate comprises:
a shelf positioned within the chilled chamber, the shelf being supported by one or more load cells.

6. The refrigerator appliance of claim 5, wherein the shelf defines a plurality of zones for receiving different food items, and wherein the controller is configured for detecting where a food item is positioned on the shelf based on the distribution of weight detected by the one or more load cells.

7. The refrigerator appliance of claim 1, wherein the inventory plate comprises a user input button for selecting a food type.

8. The refrigerator appliance of claim 1, wherein the inventory plate comprises a moisture sensor.

9. The refrigerator appliance of claim 1, comprising:
a display associated with the inventory plate, the display configured for providing an indication when food has aged a predetermined amount.

10. The refrigerator appliance of claim 9, wherein the display is a light emitting diode (LED) indicator.

11. The refrigerator appliance of claim 9, wherein the inventory plate further comprises a light sensor, and wherein the display is configured for turning off when the light sensor detects that the door has closed.

12. The refrigerator appliance of claim 1, comprising:
a timer that begins a countdown from a predetermined amount of time after a food item is placed on the inventory plate, wherein an indication is provided to a user when the timer expires.

13. A method of operating a refrigerator appliance, the refrigerator appliance comprising a cabinet defining a chilled chamber, a shelf positioned within the chilled chamber and being supported by one or more load cells, the shelf defining a plurality of zones for receiving different food items, and a door rotatably hinged to the cabinet to provide selective access to the chilled chamber, the method comprising:
receiving food items for storage on an inventory plate positioned within the chilled chamber, the inventory plate being operably coupled to a load cell;
monitoring a weight of the food items over time using the load cell;
providing an indication of food quality based at least in part on the weight of the food items; and
detecting where a food item is positioned on the shelf based on the distribution of weight detected by the one or more load cells.

14. The method of claim 13, comprising:
receiving a user input from a user input button, the user input selecting a food type of the food items being stored.

15. The method of claim 13, comprising:
monitoring a moisture level of the food items using a moisture sensor operably coupled to the inventory plate.

16. The method of claim 13, comprising:
providing an indication via a display when food has aged a predetermined amount.

17. The method of claim 16, wherein the inventory plate further comprises a light sensor, the method comprising:
turning off the display when the light sensor detects that the door has closed.

18. The method of claim 13, comprising:
initiating a timer that begins a countdown when a food item is placed on the inventory plate; and
providing an indication to a user when a predetermined amount of time has passed since the food item was placed.

19. A refrigerator appliance comprising:
a cabinet defining a chilled chamber;
a door being rotatably hinged to the cabinet to provide selective access to the chilled chamber;
an inventory plate comprising a shelf for receiving food items for storage within the chilled chamber, the shelf being supported by one or more load cells and defining a plurality of zones for receiving different food items; and
a controller operably coupled to the one or more load cells, the controller being configured for:
monitoring a weight of the food items over time using the load cell;
providing an indication of food quality based at least in part on the weight of the food items; and
detecting where a food item is positioned on the shelf based on the distribution of weight detected by the one or more load cells.

20. The refrigerator appliance of claim 19, wherein the inventory plate comprises a moisture sensor.

* * * * *